(12) United States Patent
Kudo et al.

(10) Patent No.: US 9,895,111 B2
(45) Date of Patent: Feb. 20, 2018

(54) ALARM NOTIFICATION APPARATUS, SYSTEM AND METHOD FOR DIAGNOSTIC MONITORING

(71) Applicant: FUJIFILM Corporation, Tokyo (JP)

(72) Inventors: Yuya Kudo, Tokyo (JP); Satoshi Ueda, Tokyo (JP); Hironori Matsumasa, Tokyo (JP); Ryosuke Usami, Tokyo (JP); Takamasa Yaguchi, Tokyo (JP); Yasunori Ohta, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 14/988,834

(22) Filed: Jan. 6, 2016

(65) Prior Publication Data

US 2016/0199007 A1 Jul. 14, 2016

(30) Foreign Application Priority Data

Jan. 13, 2015 (JP) ................................. 2015-004119

(51) Int. Cl.
| | | |
|---|---|---|
| *G08C 19/22* | (2006.01) | |
| *H04Q 9/00* | (2006.01) | |
| *A61B 5/00* | (2006.01) | |
| *G06F 19/00* | (2018.01) | |
| *G08B 21/04* | (2006.01) | |
| *G08B 25/08* | (2006.01) | |

(52) U.S. Cl.
CPC ............ *A61B 5/7221* (2013.01); *A61B 5/746* (2013.01); *A61B 5/747* (2013.01); *G06F 19/3406* (2013.01); *G08B 21/04* (2013.01); *G08B 25/08* (2013.01)

(58) Field of Classification Search
CPC ...................... G06F 19/322; A61B 2560/0475
USPC ..................................................... 340/870.07
See application file for complete search history.

(56) References Cited

U.S. PATENT DOCUMENTS 7,292,956 B1 * 11/2007 Guday ................ G06F 19/3487
702/118
2004/0139452 A1 * 7/2004 Hope ....................... G06F 9/542
719/318

(Continued)

FOREIGN PATENT DOCUMENTS

| JP | 2010-56895 A | 3/2010 |
| JP | 2014-54391 A | 3/2014 |

*Primary Examiner* — Fabricio R Murillo Garcia
(74) *Attorney, Agent, or Firm* — Sughrue Mion, PLLC

(57) ABSTRACT

An alarm notification apparatus includes an event detector for monitoring vital information of a body, such as a blood pressure and electrocardiogram, to check whether an anomalous event has occurred to the body. A reliability evaluator evaluates reliability of a result of detection of the anomalous event in the event detector. A notifier selects at least one addressee according to the reliability among plural predetermined addressees, and notifies the selected addressee of occurrence of the anomalous event. Preferably, a storage area is used for storing error log data expressing a false detection of an anomalous event in spite of non-occurrence of an anomalous event. Assuming that the event detector detects the anomalous event, the reliability evaluator obtains the reliability according to the error log data. Thus, it is possible to reduce influence of the false detection due to measurement artifact.

11 Claims, 12 Drawing Sheets

(56) References Cited

U.S. PATENT DOCUMENTS

2008/0046286 A1\* 2/2008 Halsted ................ G06F 19/322
  705/2
2016/0135755 A1\* 5/2016 Lu ........................ A61B 5/0022
  600/301

\* cited by examiner

FIG. 7A

MEASUREMENT DATA 3

BLOOD PRESSURE

UPPER 120 mmHg

LOWER 80 mmHg

FIG. 7B

MEASUREMENT DATA 4

BLOOD PRESSURE

UPPER 120 mmHg

LOWER 80 mmHg

ALARM

MESSAGE 2014.6.7 14:37:25
ANOMALOUS EVENT IN BLOOD
PRESSURE - PERFORM INTERVENTION

PATIENT

PATIENT A   ID: 0000   PATIENT TYPE A

ANOMALOUS EVENT

BLOOD PRESSURE         HERE

UPPER 120
      mmHg

LOWER 80
      mmHg

In case of false detection,
press register button.

REGISTER FALSE DETECTION

ALARM NOTIFICATION APPARATUS, SYSTEM AND METHOD FOR DIAGNOSTIC MONITORING

CROSS-REFERENCE TO RELATED APPLICATION

This application claims priority under 35 USC 119 from Japanese Patent Application No. 2015-004119, filed 13 Jan. 2015, the disclosure of which is incorporated by reference herein.

BACKGROUND OF THE INVENTION

1. Field of the Invention

The present invention relates to an alarm notification apparatus, system and method for diagnostic monitoring. More particularly, the present invention relates to an alarm notification apparatus, system and method for diagnostic monitoring in which a detected anomalous event in a body can be notified suitably, and a false detection during operation for the detection can be considered suitably in view of notification to an addressee.

2. Description Related to the Prior Art

A medical computer system for supporting medical services is suggested in the field of medical instruments. A medical computer system of JP-A 2014-054391 and JP-A 2010-056895 has an alarm notification apparatus, which monitors vital information (electrocardiogram, motion and posture) of a patient body, and notifies a predetermined addressee of alarm information upon detecting an anomalous event in the body. JP-A 2010-056895 also discloses a structure for not notifying information in case possibility of false detection is high even upon detecting an anomalous event.

However, wrong notification may occur in JP-A 2014-054391, as the automated detection of an anomalous event cannot remove false detections. A staff member or addressee of the wrong notification may perform wasteful action for intervention to the body. The disclosure of JP-A 2010-056895 may decrease occurrence of false detections, because of temporary interruption of the notification by estimating possibility of false detections. However, a problem arises with the construction of JP-A 2010-056895 in that occurrence of an anomalous event may be missed, as improper estimation of false detection may occur in spite of an actual occurrence of an anomalous event, so that notification is improperly interrupted.

SUMMARY OF THE INVENTION

In view of the foregoing problems, an object of the present invention is to provide an alarm notification apparatus, system and method for diagnostic monitoring in which a detected anomalous event in a body can be notified suitably, and a false detection during operation for the detection can be considered suitably in view of notification to an addressee.

In order to achieve the above and other objects and advantages of this invention, an alarm notification apparatus includes an event detector for monitoring vital information of a body, to check whether an anomalous event has occurred to the body. A reliability evaluator evaluates reliability of a result of detection of the anomalous event in the event detector. A notifier selects at least one addressee according to the reliability among plural predetermined addressees, and notifies the selected addressee of occurrence of the anomalous event.

Preferably, a reference data storage area is used for storing reference range data of a reference range of the vital information. Assuming that the vital information from the body becomes beyond the reference range, the event detector detects the occurrence of the anomalous event to the body.

Preferably, an error storage area is used for storing error log data expressing a false detection of an anomalous event in spite of non-occurrence of the anomalous event. Assuming that the event detector detects the anomalous event, the reliability evaluator obtains the reliability according to the error log data.

Preferably, the event detector outputs event record data. The reliability evaluator acquires degree of coincidence between the event record data and the error log data recorded previously by comparison thereof, sets the reliability higher according to lowness of the degree of coincidence, and sets the reliability lower according to highness of the degree of coincidence.

Preferably, the body is of a patient hospitalized in a hospital facility.

Preferably, the plural addressees include first and second addressees. The notifier performs notification to the first addressee assuming that the reliability is lower than a predetermined threshold for recognition, and performs notification to the first and second addressees assuming that the reliability is equal to or higher than the threshold.

Preferably, the first addressee is an on-site user present in a hospital facility, and the second addressee is an off-site user absent from the hospital facility.

Preferably, furthermore, a recognition unit checks whether a user terminal apparatus used by each one of the addressees is on-line with a communication network of the hospital facility, judges that the addressee is the on-site user assuming that the user terminal apparatus is on-line with the communication network, and judges that the addressee is the off-site user assuming that the user terminal apparatus is off-line from the communication network.

In another preferred embodiment, furthermore, a recognition unit acquires a current location of each one of the addressees from a user terminal apparatus used by the addressee, judges that the addressee is the on-site user assuming that the current location is inside the hospital facility, and judges that the addressee is the off-site user assuming that the current location is outside the hospital facility.

In still another preferred embodiment, the first and second addressees are medical staff members, and the second addressee is different from the first addressee in a professional category for a medical service to the patient body.

Preferably, the vital information is information of at least one of a blood pressure, electrocardiogram, heart rate, respiration rate and body temperature.

Also, an alarm notification system includes a diagnostic measurement apparatus for measuring vital information of a body, and an alarm notification apparatus for notifying occurrence of an anomalous event in the body upon the occurrence thereof according to the vital information of the body input by the diagnostic measurement apparatus. In the alarm notification system, the alarm notification apparatus includes an event detector for monitoring the vital information of the body, to check whether the anomalous event has occurred to the body. A reliability evaluator evaluates reliability of a result of detection of the anomalous event in the event detector. A notifier selects at least one addressee according to the reliability among plural predetermined addressees, and notifies the selected addressee of the occurrence of the anomalous event.

Also, an alarm notification method is provided, and includes a step of monitoring vital information of a body, to check whether an anomalous event has occurred to the body. Reliability of a result of detection of the anomalous event in the event checking step is evaluated. At least one addressee according to the reliability is selected among plural predetermined addressees, to notify the selected addressee of occurrence of the anomalous event.

Consequently, a false detection during operation for the detection can be considered suitably in view of notification to an addressee, because reliability in relation to the detection of an anomalous event is evaluated in selectively designating addressees of the notification. Thus, it is possible to reduce influence of the false detection due to measurement artifact.

BRIEF DESCRIPTION OF THE DRAWINGS

The above objects and advantages of the present invention will become more apparent from the following detailed description when read in connection with the accompanying drawings, in which:

FIGS. 7A and 7B are graphs illustrating a blood pressure with which an anomalous event occurs;

DETAILED DESCRIPTION OF THE PREFERRED EMBODIMENT(S) OF THE PRESENT INVENTION

Figure 1:
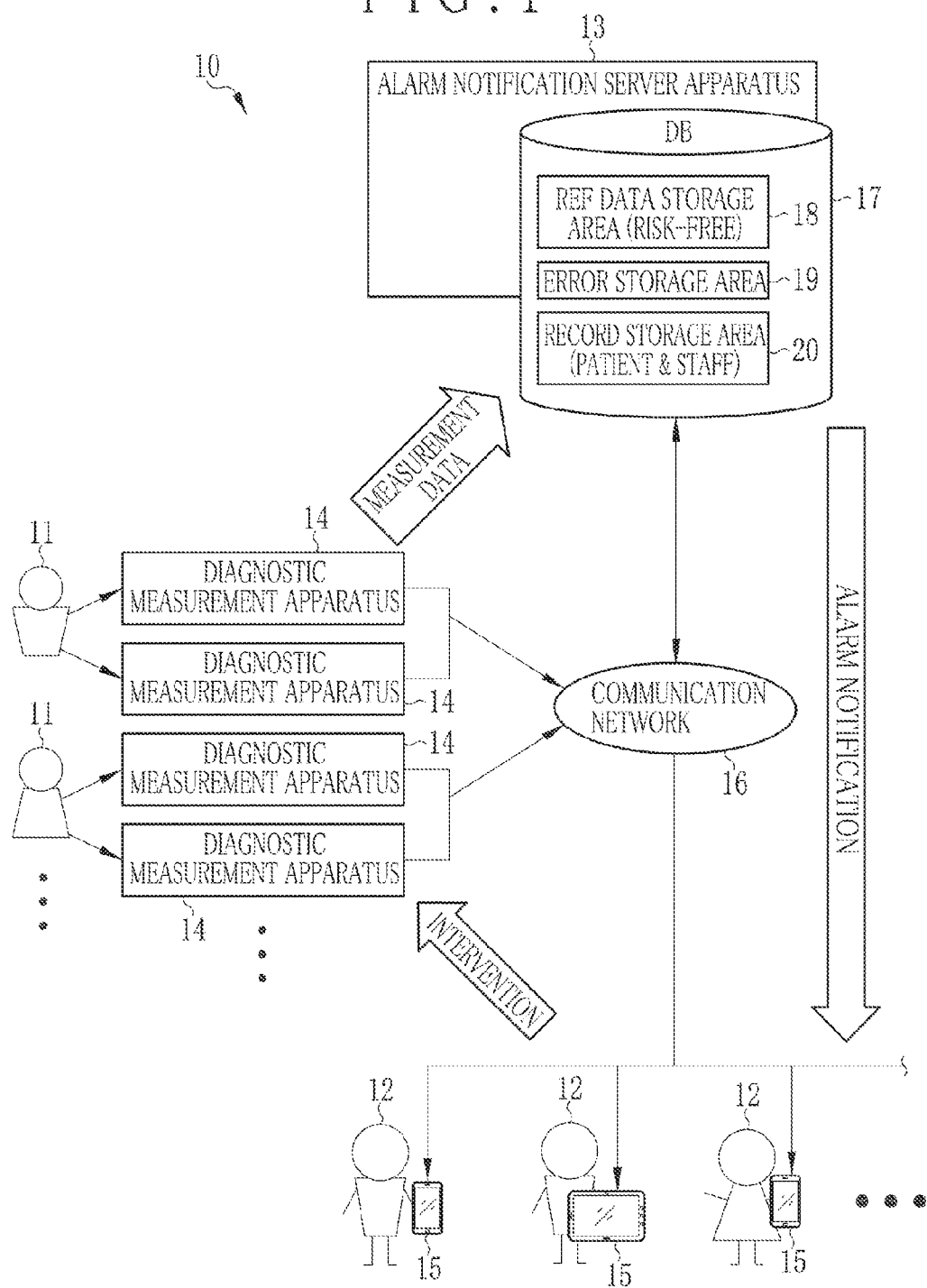
FIG. 1 is a block diagram schematically illustrating an alarm notification system.

In FIG. 1, an alarm notification system 10 is a computer system for monitoring vital information of a body, and notifying information of predetermined addressees, the information expressing detection of occurrence of an anomalous event to the body. In the embodiment, the alarm notification system 10 is used for a body 11 of an in-patient hospitalized in a hospital facility or medical facility. Assuming that an anomalous event (high risk) occurs to the body 11, the alarm notification system 10 notifies an addressee 12 of the occurrence of the anomalous event to the body 11, the addressee 12 being a user or a medical staff member (subscriber) in a medical team. Examples of the addressee 12 are a doctor, nurse, technician of radiology (radiologist) and other caregivers (clinicians) assigned with tasks for medical services to the body 11.

The alarm notification system 10 includes an alarm notification server apparatus 13, a diagnostic measurement apparatus 14 (vital information measuring device), and a user terminal apparatus 15. A communication network 16 connects those devices in a communicable manner with one another. An example of the communication network 16 is a local area network (LAN) of which an area of communicability is a site of a hospital facility 70 (See FIG. 9A).

Examples of the user terminal apparatus 15 are a tablet computer, smart phone and the like used by the addressee 12 working in the hospital facility 70. The alarm notification system 10 performs information distribution of an information page 61 of FIG. 8 to the user terminal apparatus 15, and notifies the addressee 12 of occurrence of the anomalous event by use of the user terminal apparatus 15. The user terminal apparatus 15 is automatically set communicable with the communication network 16 in the area of connection, namely in the site of the hospital facility 70. In case the user terminal apparatus 15 moves to the outside of the hospital facility 70, namely outside the area of the connection, the user terminal apparatus 15 becomes off-line from the communication network 16.

The diagnostic measurement apparatus 14 measures vital information of the body 11, for example, an electrocardiographic apparatus, heart rate meter, blood pressure monitor apparatus, respiratory measurement device and body temperature thermometer. The diagnostic measurement apparatus 14 is positioned suitably at the body 11 for the continuous measurement. Measurement data is obtained, and transmitted by the diagnostic measurement apparatus 14 to the alarm notification server apparatus 13 with the communication network 16 in a real-time control.

In short, the vital information in the present invention is information of at least one of a blood pressure, electrocardiogram, heart rate, respiration rate and body temperature.

The alarm notification server apparatus 13 detects an anomalous event of the body 11 according to vital information input by the diagnostic measurement apparatus 14, arithmetically obtains reliability of the result of the detection, and notifies addressees of the occurrence of the anomalous event selectively according to the determined reliability. An active database 17 is combined with the alarm notification server apparatus 13 for storing various data. In the active database 17, there are a reference data storage area 18 or first storage area for normality (risk-free), an error storage area 19 or second storage area, and a record storage area 20 or third storage area for patient bodies and staff members.

Figure 2:
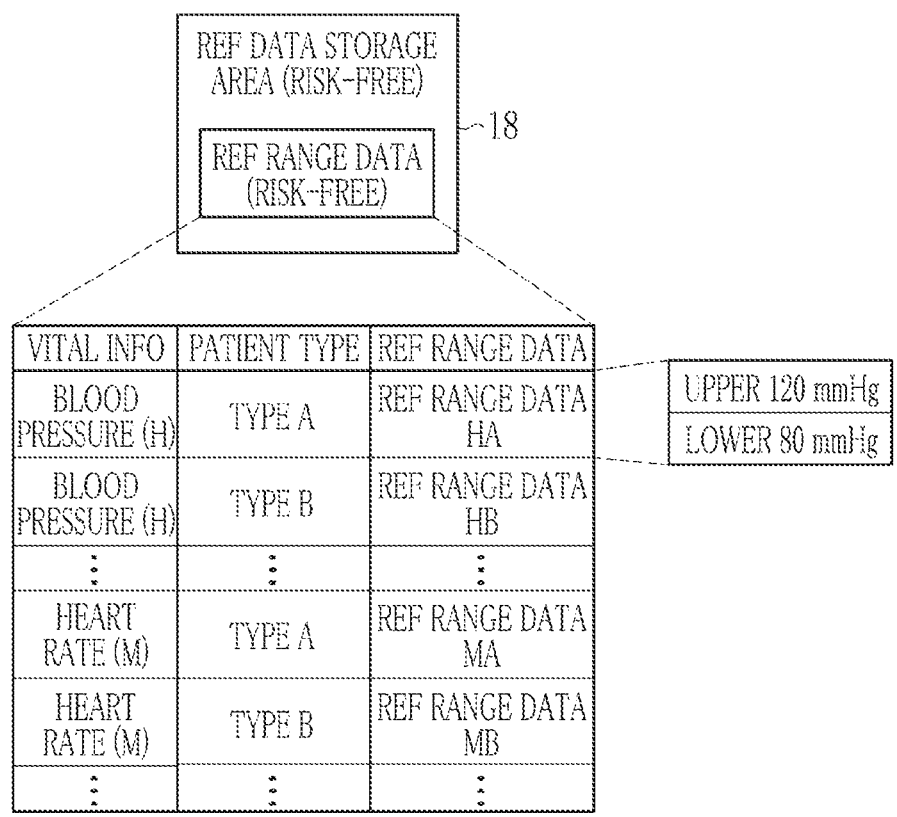
FIG. 2 is a data chart illustrating reference range data.

In FIG. 2, the reference data storage area 18 stores reference range data (normal or risk-free) of vital information. For example, the reference range data includes first and second reference range data, the first reference range data being for a blood pressure as vital information, the second reference range data being for an electrocardiogram as vital information. Also, each reference range data is classified according to a patient type or attributes of the body 11, such as age, sex, height, weight and the like. For the blood pressure as vital information, the reference range data is information of upper and lower limit values of the blood pressure. For the electrocardiogram, the reference range data includes information of waveforms of P, Q, R, S and T, wavelength, amplitude and the like.

In FIG. 2, reference range data HA is data for the blood pressure of the body 11 in a patient type A. In the embodiment, a reference range according to the embodiment is 80-120 mmHg. Reference range data HB is data for the blood pressure of a body 11 in a patient type B. Reference range data MA is data for a heart rate of the body 11 in the patient type A. Reference range data MB is data for a heart rate of the body 11 in the patient type B.

Figure 3:
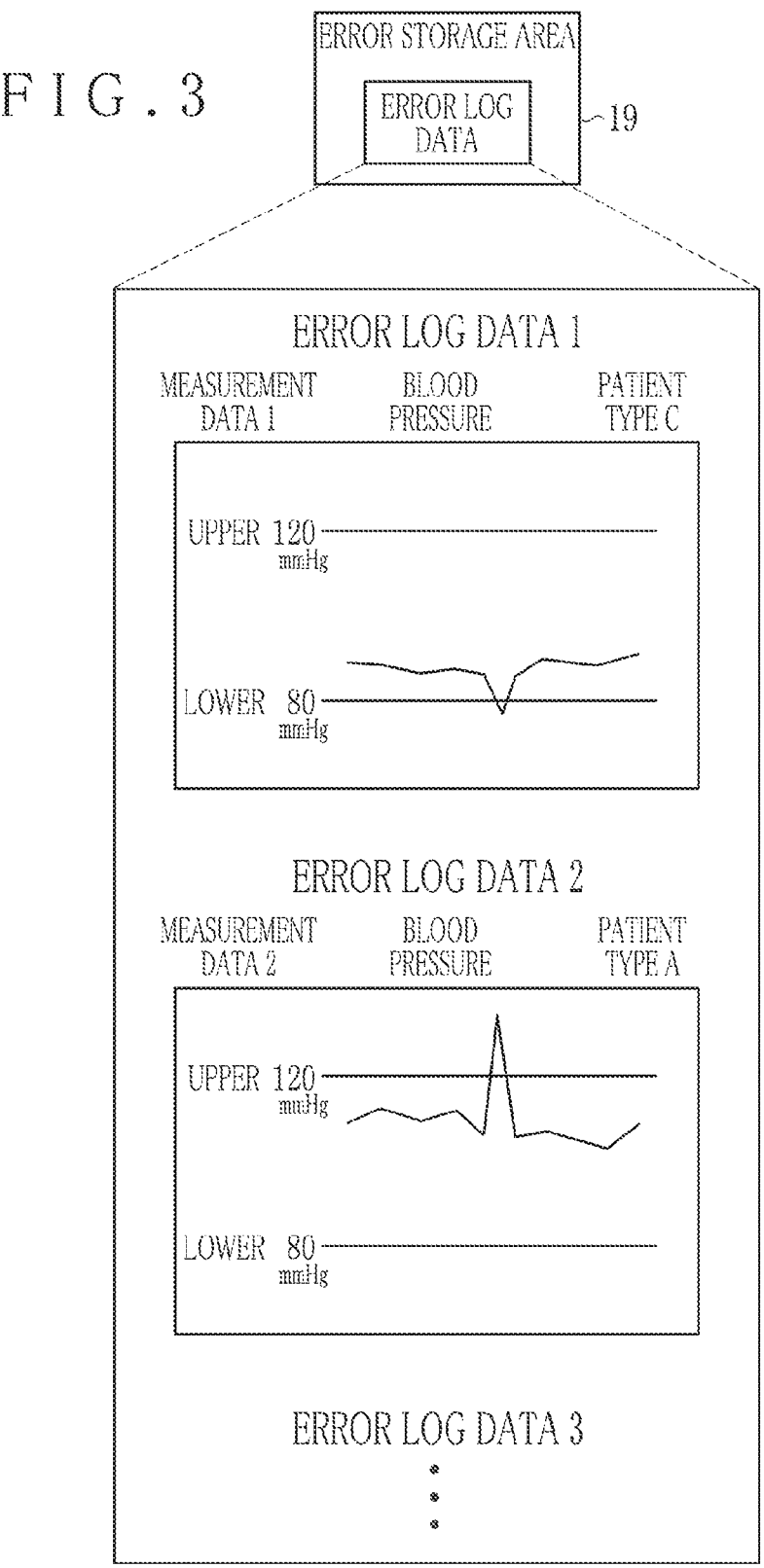
FIG. 3 is a data chart illustrating error log data.

In FIG. 3, the error storage area 19 stores error log data. The error log data is data of a false detection or incidental detection of an anomalous event in spite of lack of such an anomalous event. The error log data is classified for types of the vital information or attributes of the body 11 upon occurrence of false detection for measurement data of the vital information at the time of the detection or before and after the detection. Upon each time of the occurrence of the false detection, one item of error log data is created and stored to the error storage area 19.

In FIG. 3, error log data 1 expresses occurrence of a false detection (error) of an anomalous event in measurement data 1 of a measured blood pressure of the body 11 of a patient type C. In the error log data 1, detection of an anomalous event has occurred upon a drop of the blood pressure under a lower limit. However, a reason of the anomalous event is an artifact, such as misoperation of the measurement or a temporary motion of the body 11 during the measurement. Thus, a state of the body 11 is stable (normal or low-risk) in spite of the incidental detection.

Also, error log data 2 expresses occurrence of a false detection (error) of an anomalous event in measurement data 2 of a measured blood pressure of the body 11 of the patient type A. In the error log data 2, detection of an anomalous event has occurred upon a rise of the blood pressure over an upper limit. However, a reason of the anomalous event is an artifact during the measurement. Thus, a state of the body 11 is stable (normal or low-risk) in spite of the incidental detection.

Figure 4:
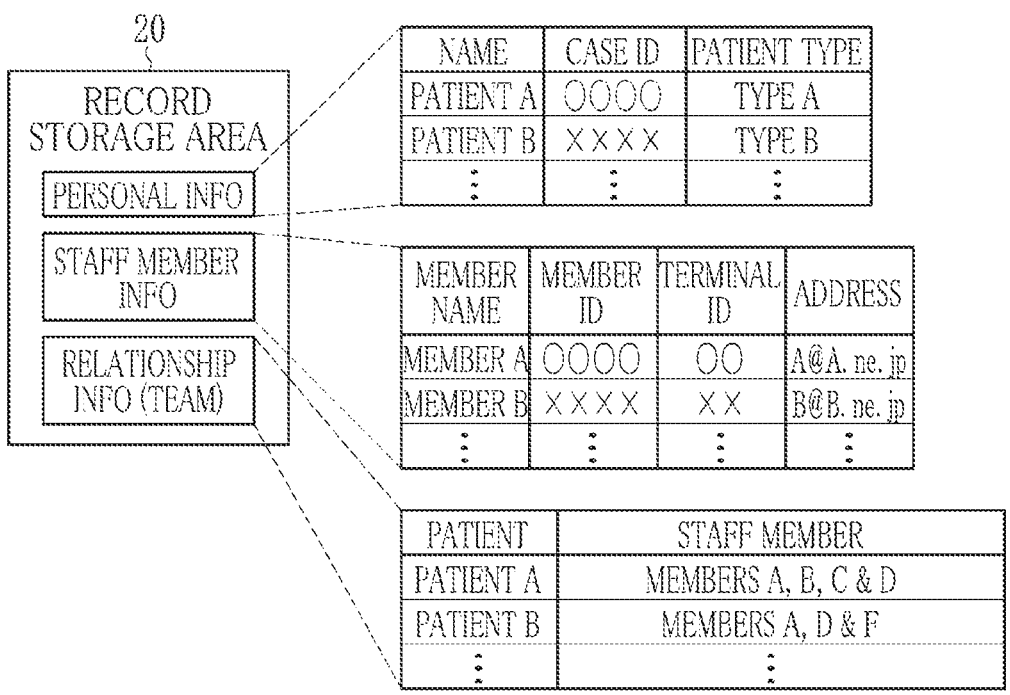
FIG. 4 is a data chart illustrating personal information, staff member information and relationship information.

In FIG. 4, the record storage area 20 stores personal information, staff member information and relationship information (medical team information). The personal information is associated with respectively the body 11, and includes a name, case ID, patient type and the like of the body 11. The staff member information is associated with respectively the addressees 12, and includes a member name, member ID and the like of the addressees 12, and a terminal ID, electronic address and the like of the user terminal apparatuses 15 used by the addressees 12. The relationship information (medical team information) is data of a look-up table, as a combination of the body 11 and his or her relevant staff members among the addressees 12, and is referred to for the alarm notification server apparatus 13 to select the addressees of notification of an anomalous event.

The alarm notification server apparatus 13 is constituted by a computer and programs installed therein. Examples of the computer are a personal computer, server computer, workstation and the like. The programs include control programs and application programs. The control programs are an Operating System (OS) and the like. The application programs are client programs, server programs and the like.

Figure 5:
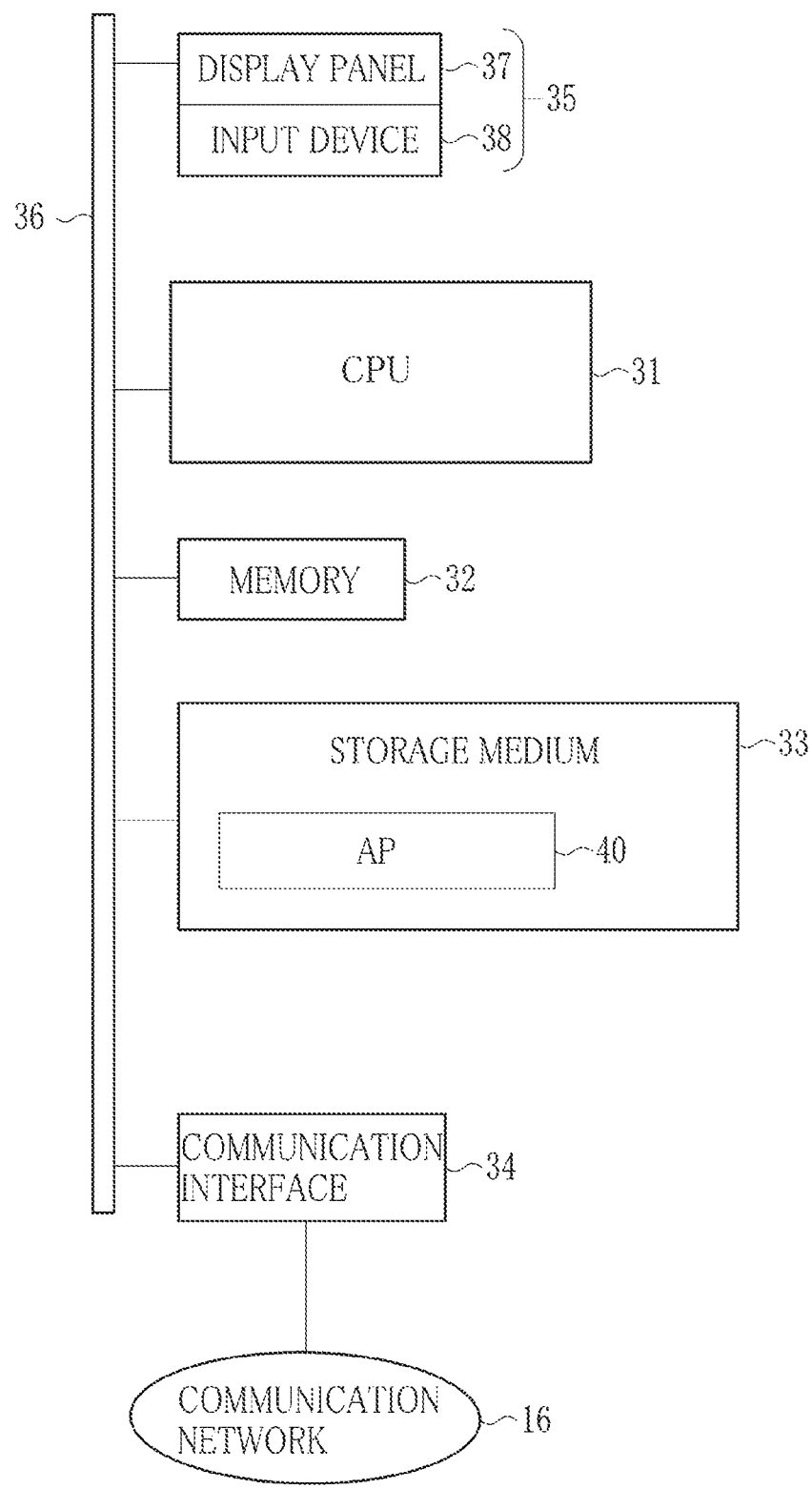
FIG. 5 is a block diagram schematically illustrating an alarm notification server apparatus.

In FIG. 5, the computer constituting the alarm notification server apparatus 13 includes a CPU 31 (central processing unit), a non-transitory memory 32, a non-transitory storage medium 33 or storage device, a communication interface 34 and a user interface 35 for input/output. A data bus 36 in the alarm notification server apparatus 13 interconnects those circuit devices. The user interface 35 includes a display panel 37 and an input device 38, of which examples are a keyboard, mouse and the like.

An example of the storage medium 33 is a hard disk drive or HDD. An application program 40 as a computer-executable program is stored in the storage medium 33. Also, a disk array having plural HDDs is combined with each of the alarm notification server apparatus 13 by way of the storage medium 33 for the active database 17 but separately from the HDD for the program. Note that the disk array can be contained in a server main unit of the alarm notification server apparatus 13, but can be externally connected to the server main unit by use of the local area network or LAN as a network.

The memory 32 is a working memory with which the CPU 31 performs tasks, for example, RAM (random access memory). The CPU 31 reads the control program from the storage medium 33, and loads the memory 32 with the control program, to control various elements in the computer by running the control program. The communication interface 34 is a network interface for controlling transmission by use of the communication network 16.

Figure 6:
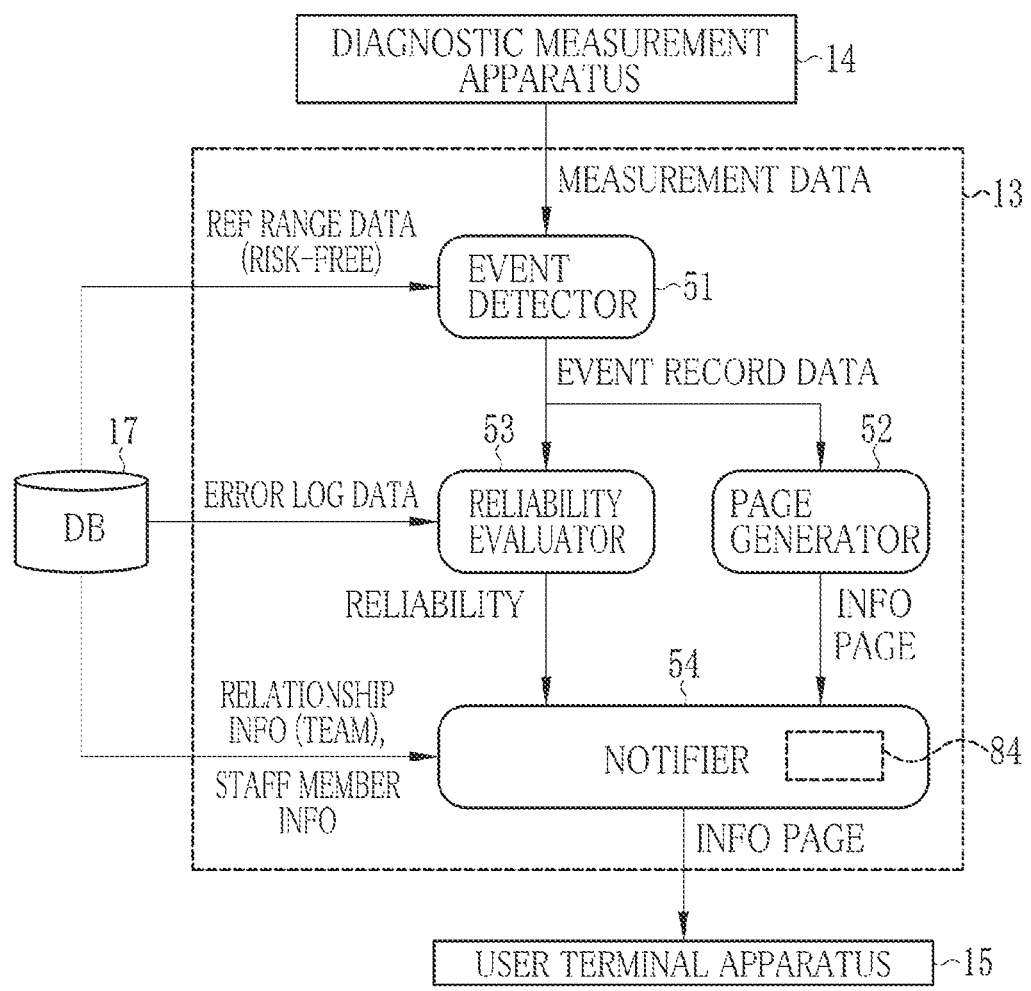
FIG. 6 is a block diagram schematically illustrating circuit devices in the alarm notification server apparatus.

In FIG. 6, the server program is installed in the alarm notification server apparatus 13 by way of the application program 40. The CPU 31 in the alarm notification server apparatus 13 is caused by running the server program to cooperate with the memory 32, to function an event detector 51, a page generator 52, a reliability evaluator 53 and a notifier 54.

The diagnostic measurement apparatus 14 inputs vital information of the body 11, namely measurement data, to the event detector 51. The event detector 51 reads out risk-free reference range data corresponding to the input measurement data from the reference data storage area 18 in the active database 17, compares the measurement data with the reference range data, and checks whether the measurement data is beyond the range of the reference range data. Assuming that the measurement data is beyond the range of the reference range data, it is judged that an anomalous event has occurred to the body 11 corresponding to the measurement data. For example, an anomalous event is detected with measurement data 3 of FIG. 7A with the blood pressure decreased under the lower limit. Also, an anomalous event is detected with measurement data 4 of FIG. 7B with the blood pressure increased over the upper limit.

In FIG. 6, the event detector 51 operates upon detection of occurrence of an anomalous event, and creates event record data by associating relevant information with measurement data at the time of detection and before and after the detection (for example, in a period of one minute), the relevant information including information of a type of the vital information and personal information of the body 11. The event detector 51 inputs the event record data to the page generator 52 and the reliability evaluator 53. As the measurement data is input by the diagnostic measurement apparatus 14 in the real-time control as described above, performance of the event detector 51 for detecting an anomalous event and inputting to the page generator 52 and the reliability evaluator 53 is carried out in the real-time control.

In the embodiment, an anomalous event is detected by comparison between the measurement data input by the diagnostic measurement apparatus 14 and the reference data for normality (risk-free) read from the reference data storage area 18. However, some type of the diagnostic measurement apparatus 14 has a function for detecting an anomalous event. In the alarm notification system 10 inclusive of this type of the diagnostic measurement apparatus 14, the function for detecting an anomalous event can be omitted from the alarm notification server apparatus 13. In this structure, occurrence of a detected anomalous event is notified to the alarm notification server apparatus 13 upon detecting the anomalous event in the diagnostic measurement apparatus 14. In response, the alarm notification server apparatus 13 associates the measurement data in a predetermined period beginning before the detection and ending after the detection with information including the type of the vital information and personal information of the body 11, so as to generate event record data.

Figure 8:
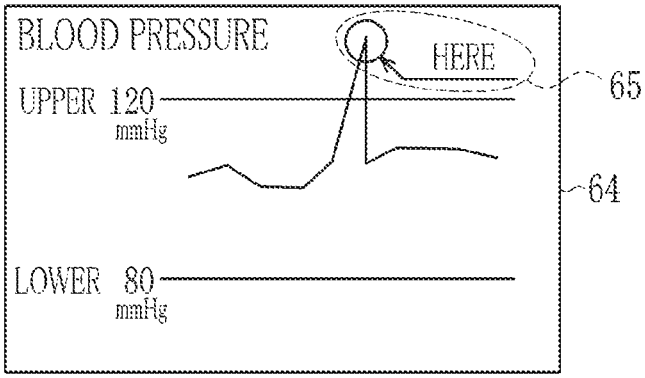
FIG. 8 is a front elevation illustrating an information page.

The page generator 52 upon receiving event record data from the event detector 51 creates the information page 61 of FIG. 8 for notification according to the event record data and sets the information page 61 in the notifier 54.

In FIG. 8, the information page 61 includes an area for message information 62, an area for personal information 63, and an area for measurement data 64. The message information is a message of occurrence of an anomalous event or request for intervention to the anomalous event. The personal information is information of the body 11. The area for the measurement data 64 displays the measurement data input by the event detector 51. A visual indicator 65 is displayed in the area for the measurement data 64 for emphasizing a location of detection of the anomalous event, for example, arrow, balloon and the like. In FIG. 8, the information page 61 is created upon receiving an input of the measurement data 4 of FIG. 7B from the diagnostic measurement apparatus 14.

An error register button 66 is disposed in the information page 61 for input action in the case of false detection of the notified anomalous event. As will be described later, the information page 61 is output to the user terminal apparatus 15 and displayed on a display of the user terminal apparatus 15. The addressee 12 using the user terminal apparatus 15 monitors an anomalous event of the body 11 according to the information page 61, and is ready for medical intervention (care). It is incidentally likely that the progress of the body 11 is stable (normal or low-risk) without anomaly, and that the notification of the information page 61 is based on false detection of an anomalous event. For this situation, the error register button 66 is operated.

In case the error register button 66 is operated, a request for reporting a false detection (error) is transmitted from the user terminal apparatus 15 to the alarm notification server apparatus 13. The alarm notification server apparatus 13 responsively registers error log data of the false detection. Specifically, the error log data displayed in the information page 61 is stored to the error storage area 19 as new error log data. Then the reliability is arithmetically obtained by use of the error log data registered one after another.

In FIG. 6, the reliability evaluator 53 upon receiving event record data from the event detector 51 compares the event record data with the error log data read from the error storage area 19 of the active database 17 to obtain values of the degree of coincidence between those, and selectively reads one of the values of the degree of coincidence being obtained. The values of the degree of coincidence express information of coincidence of the event record data with the error log data with reference to the error log data, for example, as high as 90%.

Thus, the degree of coincidence is information of nearness between the event record data and the error log data. Possibility of a false detection in the detected anomalous event from the event detector 51 is higher according to highness of the degree of coincidence, but is lower according to lowness of the degree of coincidence. Consequently, reliability in the result of detecting the anomalous event from the event detector 51 is lower according to highness of the degree of coincidence, and is higher according to lowness of the degree of coincidence.

The reliability evaluator 53 determines reliability of a result of detecting the anomalous event from the event detector 51 so as to decrease reliability according to an increase in the degree of coincidence and to increase the reliability according to a decrease in the degree of coincidence. In the embodiment, the reliability is obtained from reliability (%)=100(%)−degree of coincidence (%). For example, the reliability is 10% assuming that the highest degree of coincidence between the error log data and the event record data is 90%. The reliability evaluator 53 inputs the reliability to the notifier 54.

The notifier 54 upon receiving the input of the reliability judges a rank of the reliability from the predetermined ranks of "high" and "low". To this end, the input reliability is compared with a threshold, for example, 80%. Assuming that the reliability is equal to or more than the threshold, it is judged that the reliability is high. Assuming that the reliability is less than the threshold, it is judged that the reliability is low.

For example, let an anomalous event be detected according to the measurement data 3 in FIG. 7A. The measurement data 3 of an anomalous event expresses a gradual decrease in the blood pressure and a continuous decrease even after the decrease under a lower limit. Error log data, of which degree of coincidence is the highest with the measurement data 3 among the error log data, is the error log data 1 or the measurement data 1, because of its lower level than the lower limit. However, the measurement data 1 expresses an abrupt (temporary) drop of the blood pressure under the lower limit, and does not express a continuous drop of the blood pressure under the lower limit in the manner of the measurement data 3. Thus, the degree of coincidence between the error log data 1 and the event record data is low, for example, as low as 10%. The reliability in detecting an anomalous event becomes higher, for example, as high as 90%. In conclusion, the reliability in detecting the anomalous event is judged to be high in the case of detecting the anomalous event on the basis of the measurement data 3, as no artifact is related.

Assuming that an anomalous event is detected according to the measurement data 4 in FIG. 7B, it is found that the measurement data 4 (event record data) is based on an abrupt increase of the blood pressure over an upper limit. In FIG. 3, error log data, of which degree of coincidence with the measurement data 4 is the highest among the various error log data, is the error log data 2 (measurement data 2). Also, it is found that the measurement data 2 is based on an abrupt increase of the blood pressure over the upper limit. Therefore, the degree of coincidence between the error log data 2 and the event record data is high, for example, as high as 70%. The reliability in detecting the anomalous event becomes lower, for example, as low as 30%. In conclusion, the reliability in detecting the anomalous event is judged to be low in the case of detecting the anomalous event on the basis of the measurement data 4, because of an artifact.

Figure 9:
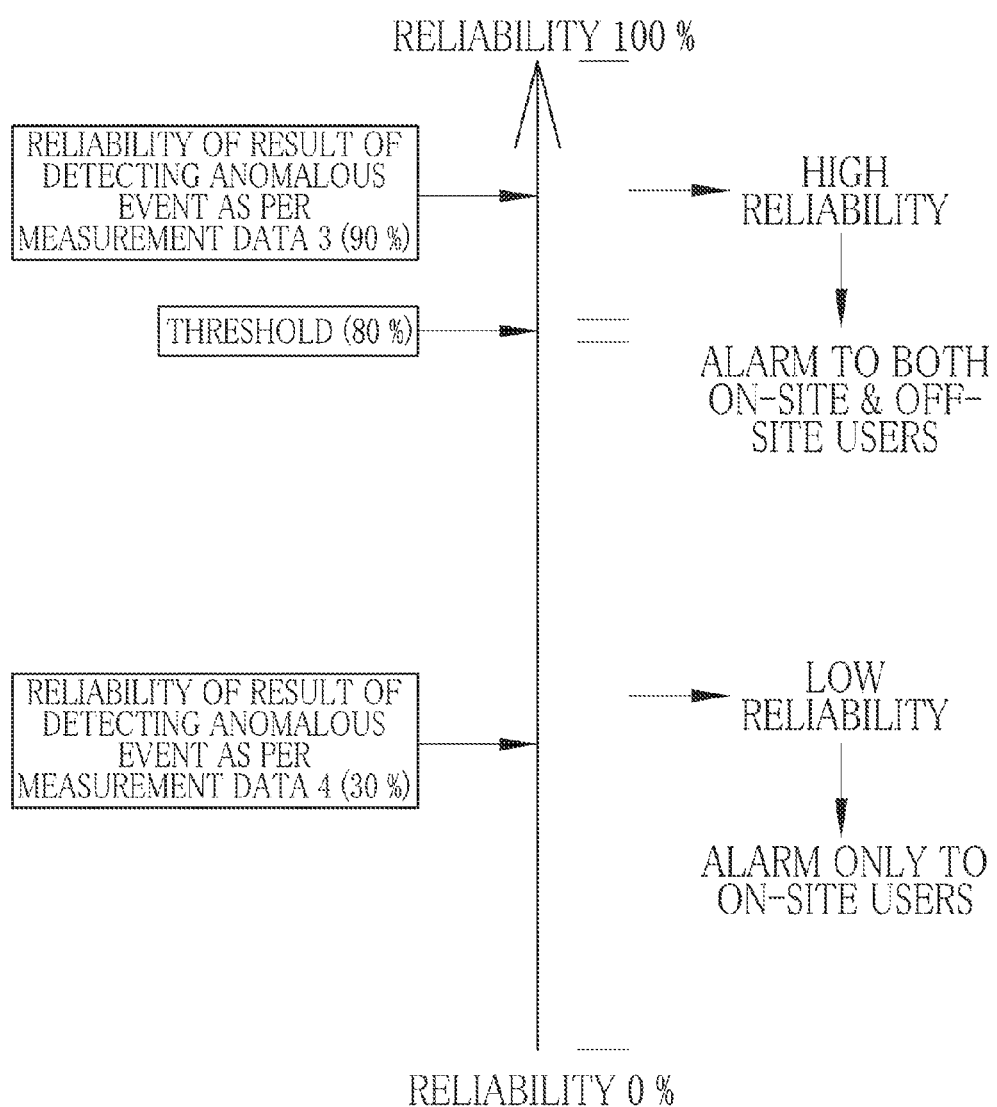
FIG. 9 is an explanatory view illustrating a relationship between reliability and selection of addressees.

Assuming that high reliability of the result of detecting an anomalous event is judged, for example, judged according to the measurement data 3, the notifier 54 in FIG. 9 performs information distribution of the information page 61 to the user terminal apparatuses 15 of all the addressees 12 (on-site and off-site) in the medical team for the body 11. The information page 61 after the information distribution is displayed in each display panel of the user terminal apparatuses 15 as addressees.

In the active database 17, the record storage area 20 stores information of a relationship between the body 11 and the addressees 12 in the medical team for the body 11, and information of the user terminal apparatuses 15 used by the addressees 12. The notifier 54 specifies the user terminal apparatus 15 of an addressee of the information page 61 by readout from the active database 17. It is likely that one of the addressees 12 being specified is off-line from the communication network 16 because the user terminal apparatus 15 is located outside an area of communicability with the communication network 16 for the reason of homecoming or holiday of the addressee 12. Then the notifier 54 utilizes a network other than the communication network 16, for example, the Internet, and performs information distribution of the information page 61 to the user terminal apparatus 15 of the addressee 12 being specified.

Figure 9A:
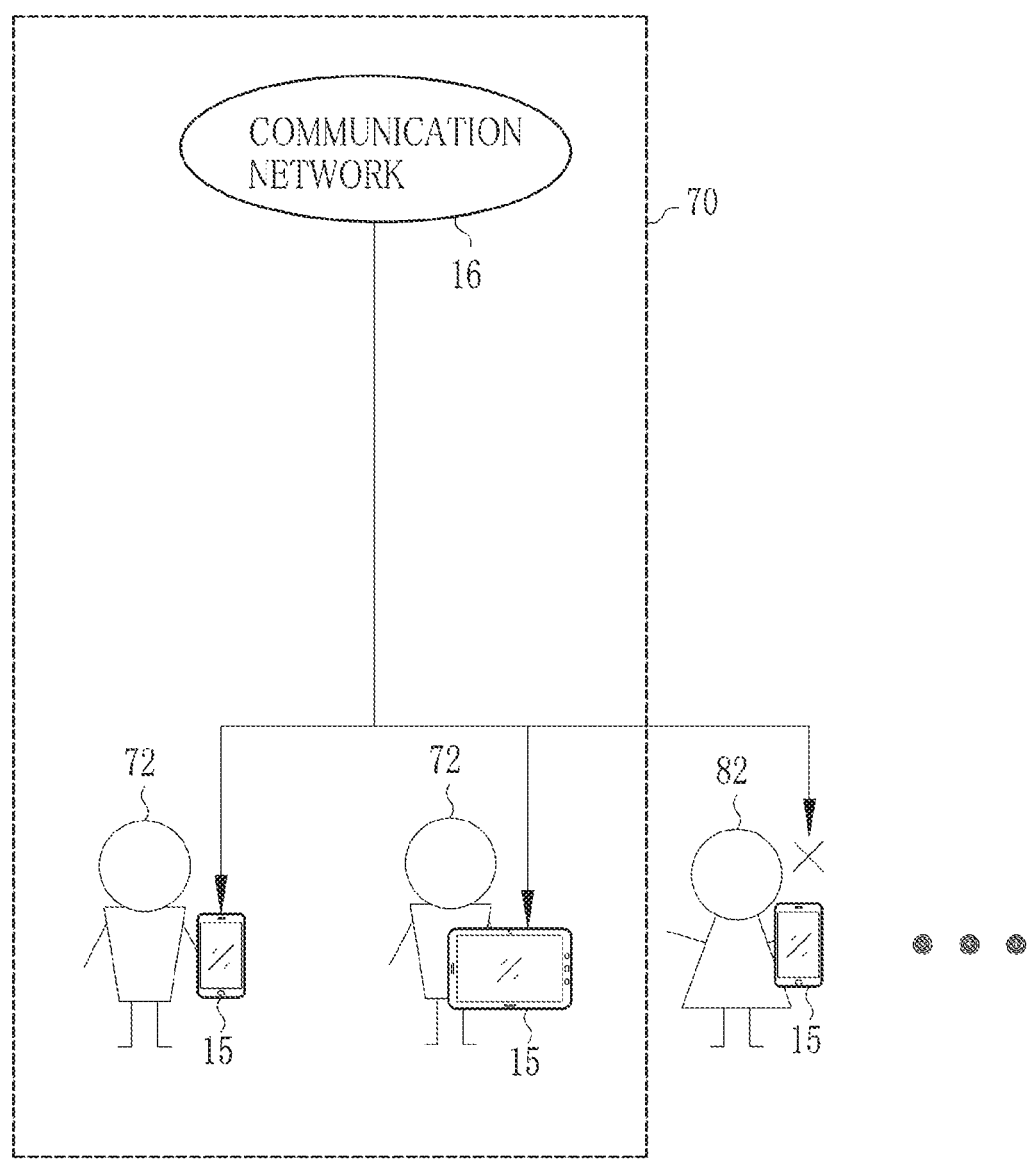
FIG. 9A is a block diagram schematically illustrating user terminal apparatuses in combination with a network of a hospital facility.

Assuming that low reliability of the result of detecting an anomalous event is judged, for example, upon detecting an anomalous event according to the measurement data 4, the notifier 54 checks which of an on-site user 72 and an off-site user 82 each of the addressees 12 is in the medical team for the body 11, as illustrated in FIG. 9A. The on-site user 72 is located in the hospital facility 70. The off-site user 82 is located outside the hospital facility 70. The notifier 54 checks whether the user terminal apparatus 15 used by the addressee 12 for medical care of the body 11 is on-line with the communication network 16 or not. It is judged that the addressee 12 using the user terminal apparatus 15 on-line with the communication network 16 is the on-site user 72, and that the addressee 12 using the user terminal apparatus 15 off-line from the communication network 16 is the off-site user 82. The notifier 54 has a recognition unit 84 for checking which of the on-site user 72 and the off-site user 82 the addressee 12 is in relation to medical care of the body 11 after detecting an anomalous event.

Assuming that low reliability is judged, the notifier 54 performs information distribution of the information page 61 only to the user terminal apparatus 15 used by the on-site user 72. The information page 61 is displayed in the user terminal apparatus 15 used by the on-site user 72 among the addressees 12.

Figure 10:
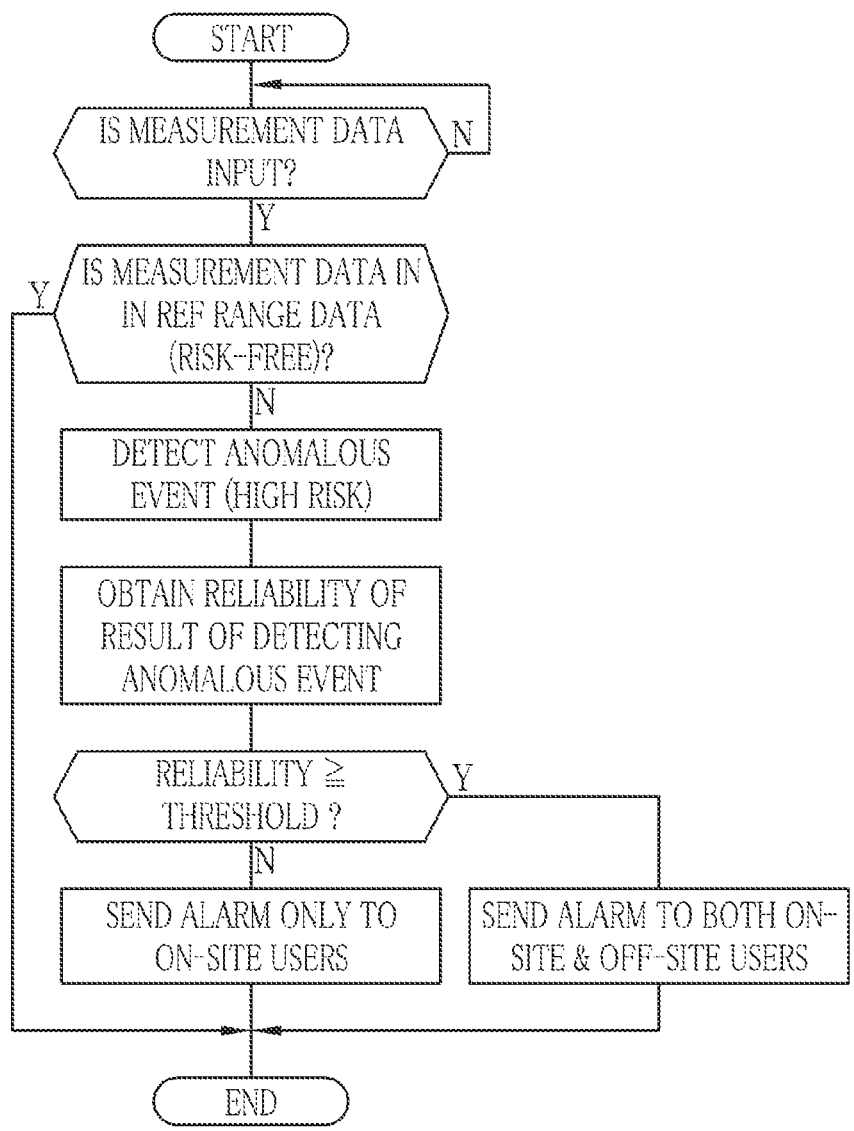
FIG. 10 is a flow chart illustrating a flow of selecting the addressees.

The operation of the above construction is described now. In FIG. 10, the alarm notification server apparatus 13, upon receiving measurement data from the diagnostic measurement apparatus 14, checks whether the measurement data is in a range of the reference range data read from the reference data storage area 18 of the active database 17. Assuming that it is judged that the measurement data is not in the range of the reference range data, the alarm notification server apparatus 13 detects that an anomalous event has occurred to the body 11 in association with the measurement data.

Upon detecting occurrence of an anomalous event, the alarm notification server apparatus 13 compares the event record data, namely the measurement data upon the detection, with the error log data read from the error storage area 19 in the active database 17, and determines information of degree of coincidence, so as to determine reliability of the anomalous event detection according to the determined degree of coincidence. Assuming that the obtained reliability is equal to or more than the threshold, namely, assuming that the reliability is "high", then the user terminal apparatuses 15 of all of the addressees 12 in the medical team for the body 11 are specified, so that the alarm notification server apparatus 13 notifies the addressees of the occurrence of the anomalous event by information distribution of the information page 61.

Assuming that the obtained reliability is less than the threshold, namely, assuming that the reliability is "low", then the user terminal apparatus 15 of the on-site user 72 in the hospital facility 70 is specified selectively in the medical team for an addressee, so that the alarm notification server apparatus 13 notifies the on-site user 72 of the occurrence of the anomalous event by information distribution of the information page 61. The alarm notification server apparatus 13 does not notify the occurrence of the anomalous event to the user terminal apparatus 15 of the off-site user 82 outside the hospital facility 70.

Thus, the alarm notification system 10 does not perform notification to the off-site user 82 absent from the hospital facility 70 because of homecoming or holidays on the condition of low reliability in the result of detecting an anomalous event. It is possible in the alarm notification system 10 to prevent unwanted influence of a false detection (error) in comparison with notification to all the staff members in the medical team for medical care of the patient body without considering reliability in a result of detecting an anomalous event. In short, detection information according to a false detection is not notified to the off-site user 82 on the condition of low reliability in the result of detecting an anomalous event. This is effective in preventing useless action of the off-site user 82 in response to the false detection.

In the alarm notification system 10, the on-site user 72 is notified of the occurrence of detection of an anomalous event even assuming that the reliability of a detection result of an anomalous event is low. The on-site user 72 can be prevented from missing the occurrence of the anomalous event unlike a technique without notification in the case of low reliability of a detection result of an anomalous event.

The present invention is not limited to the embodiments. Details of the structure can be changed suitably. For example, an anomalous event of the body 11 hospitalized in the hospital facility 70 is detected by monitoring the vital information. However, the body is not limited to that of the in-patient, but can be of an out-patient frequently visiting the hospital facility 70, or a bedridden patient in his or her home without hospitalization. In such a remote state of the body from the hospital facility 70, vital information from the diagnostic measurement apparatus 14 can be transmitted to the event detector on-line, with the Internet or network other than the communication network 16. A body to be monitored in the invention is not limited to a patient body, but can be a client or aged person cared in an elderly care facility or nursing facility.

In the above embodiments, the on-site user 72 or the off-site user 82 is recognized by checking connection with the communication network 16. However, the invention is not limited. For example, a GPS function (Global Positioning System) can be provided in the user terminal apparatus 15. A current location is detected by the GPS in the user terminal apparatus 15, and collected by the alarm notification server apparatus 13, so that the on-site user 72 and the off-site user 82 among the addressees 12 can be recognized according to the current location of the user terminal apparatus 15.

In the embodiment, both of the on-site user 72 and the off-site user 82 are notified of the anomalous event assuming that the reliability in detecting anomalous events is high. Only the on-site user 72 is notified of the anomalous event assuming that the reliability in detecting anomalous events is low. However, a relationship between the reliability in detecting anomalous events and selection of addressees of the anomalous event can be determined suitably in other manners. For example, all the relevant staff members in the medical team can be notified of an anomalous event assuming that the reliability in detecting anomalous events is high. Only nurses in the medical team for the patient body can be notified of the anomalous event assuming that the reliability in detecting anomalous events is low.

Figure 11:
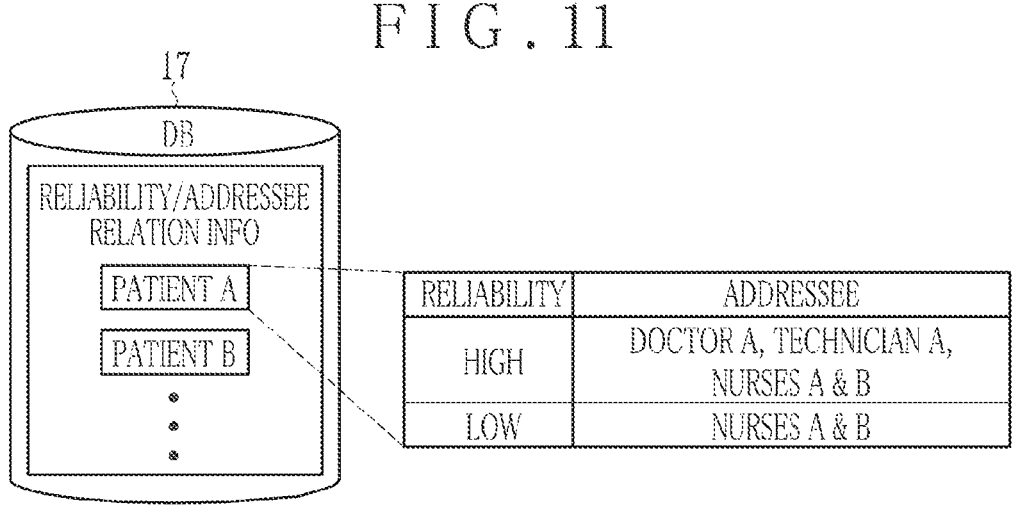
FIG. 11 is a data chart illustrating the addressees in combination with the reliability.

In FIG. 11, the active database 17 is caused to store reliability/addressee relation information (priority information). The reliability/addressee relation information is information of a look-up table of a relationship between reliability and addressees, and is referred to by the notifier 54 for selection of the addressees. The reliability/addressee relation information is associated with each one of patient bodies. In FIG. 11, all of the staff members (first and second addressees) in the medical team for the patient body A are designated assuming that the reliability of the detection result of an anomalous event is judged to be high. However, only nurses (first addressees) in the medical team for the patient body A are selected among the doctors, technicians and nurses who are different in a professional category for medical services, assuming that the reliability of the detection result of an anomalous event is judged to be low.

Figure 12:
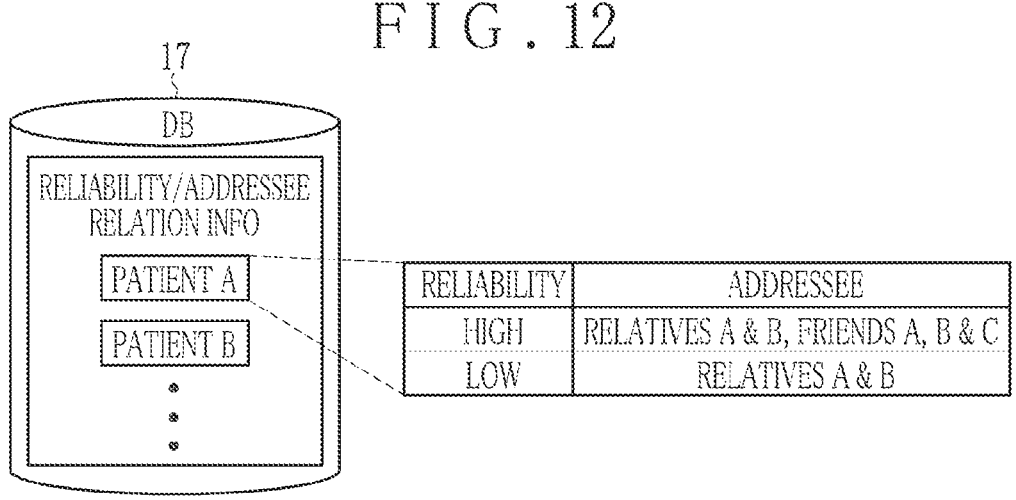
FIG. 12 is a data chart illustrating another preferred embodiment in which addressees are family members and friends.

Furthermore, addressees of the notification are not limited to medical staff members. In FIG. 12, another preferred embodiment is illustrated. Assuming that high reliability is judged for the reliability of the anomalous event detection, the occurrence of the anomalous event can be notified to family members and relatives of a patient, and friends (acquaintances) of the patient. Assuming that low reliability is judged for the reliability of the anomalous event detection, the occurrence of the anomalous event can be notified to only the family members and relatives of the patient. Elements similar to those of the above embodiments are designated with identical reference numerals in FIGS. 11 and 12.

In the above embodiments, the active database 17 stores the personal information, staff member information and relationship information. However, another database may be installed in the hospital facility 70 and can store the personal information, staff member information and relationship information (medical team information), for example, an electronic chart database for storing electronic charts. It is possible to store the information in the existing database, and to perform access to the existing database without readout from the active database 17.

The present invention is not limited to the above embodiments in which only the measurement data of the vital information of a detected anomalous event is displayed. For example, it is possible to display measurement data of the vital information after detecting an anomalous event and also measurement data of the vital information without anomaly (without detecting an anomalous event) simultaneously on the information page 61. Also, a live image can be displayed in the information page 61 by use of a live camera positioned in a hospital room or surgical operating room for the patient body in which an anomalous event is detected.

In the above embodiments, the reliability of the detection result of an anomalous event is determined without considering vital information other than vital information of the anomalous event. However, the invention is not limited. It is possible to consider measurement data of other vital information in addition to the vital information of the anomalous event, to determine reliability of the detection result of the anomalous event. For example, there is a patient body of which blood pressure is anomalous with an increase over a reference range but an electrocardiogram is not anomalous (in the reference range). For this patient body, the reliability can be set low. There is another patient body of which blood pressure is anomalous with an increase over the reference range and an electrocardiogram is anomalous. For this patient body, the reliability can be set high. In short, determination of the reliability can be performed with higher precision.

In the above embodiments, the ranks of the reliability are the two including high and low. However, the invention is not limited. For example, ranks of the reliability may be three two including high, medium and low, so that three modes of combinations of addressees can be selectively designated with priority according to a result of the anomalous event detection. Furthermore, the number of ranks of the reliability can be four or more.

In the above embodiments, the event record data in the information page 61 is stored in the error storage area 19 as error log data upon operation of the error register button 66 in the information page 61. However, it is possible automatically to recognize an extremely low level of the reliability of the detection result of an anomalous event, for example, as low as 5% or less, and to store the event record data in the error storage area 19 automatically as error log data without using the error register button 66.

The present invention is not limited to the above embodiments. Various features of the embodiments and variants of the invention can be combined with each other suitably. Also, the computer-executable program and a storage medium for storing the computer-executable program are included in the scope of the present invention.

According to one embodiment mode of the invention, a non-transitory computer readable medium for storing a computer-executable program is provided, the computer-executable program enabling execution of computer instructions to perform operations for alarm notification. The operations include monitoring vital information of a body, to check whether an anomalous event has occurred to the body. The operations include evaluating reliability of a result of detection of the anomalous event in the event checking step. The operations include selecting at least one addressee according to the reliability among plural predetermined addressees, to notify the selected addressee of occurrence of the anomalous event.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An alarm notification apparatus comprising:
a processor configured to perform the functions of:
monitoring vital information of a patient body, to check whether an anomalous event has occurred to said patient body;
evaluating reliability of a result of detection of said anomalous event in said monitoring vital information function; and
selecting at least one addressee according to said reliability among plural predetermined addressees, and notifying said selected addressee of occurrence of said anomalous event; and an error storage for storing error log data indicating a false detection when the anomalous event has not actually occurred, but where the monitoring vital information function indicates occurrence of the anomalous event, wherein in a case where said monitoring vital information function detects said anomalous event, said evaluating reliability function obtains said reliability according to said error log data, wherein said monitoring vital information function outputs medical event record data, and wherein said evaluating reliability function acquires degree of coincidence between said medical event record data and said error log data recorded previously by comparison thereof, sets said reliability higher according to lowness of said degree of coincidence, and sets said reliability lower according to highness of said degree of coincidence.

2. The alarm notification apparatus as defined in claim 1, wherein a reference data storage area is used for storing reference range data of a reference range of said vital information;

wherein in a case where said vital information from said patient body becomes beyond said reference range, said monitoring vital information function detects said occurrence of said anomalous event to the patient body.

3. The alarm notification apparatus as defined in claim 1, wherein said patient body is of a patient hospitalized in a hospital facility.

4. The alarm notification apparatus as defined in claim 1, wherein said plural addressees include first and second addressees;

said notifying function further performs notification to said first addressee in a case where said reliability is lower than a predetermined threshold for recognition, and performs notification to said first and second addressees in a case where said reliability is equal to or higher than said threshold.

5. The alarm notification apparatus as defined in claim 4, wherein said first addressee is an on-site user present in a hospital facility, and said second addressee is an off-site user absent from said hospital facility.

6. The alarm notification apparatus as defined in claim 5, the processor further configured to check whether a user terminal apparatus used by each one of said plural predetermined addressees is on-line with a communication network of said hospital facility, to judge that one of said plural predetermined addressees is said on-site user in a case where said user terminal apparatus is on-line with said communication network, and to judge that another one of said plural predetermined addressees is said off-site user in a case where said user terminal apparatus is off-line from said communication network.

7. The alarm notification apparatus as defined in claim 5, the processor further configured to acquire a current location of each one of said plural predetermined addressees from a user terminal apparatus used by each one of said plural predetermined addressees, to judge that one of said plural predetermined addressees is said on-site user in a case where said current location is inside said hospital facility, and to judge that another one of said plural predetermined addressees is said off-site user in a case where said current location is outside said hospital facility.

8. The alarm notification apparatus as defined in claim 4, wherein said first and second addressees are medical staff members, and said second addressee is different from said first addressee in a professional category for a medical service to the patient body.

9. The alarm notification apparatus as defined in claim 1, wherein said vital information is information of at least one of a blood pressure, electrocardiogram, heart rate, respiration rate and body temperature.

10. An alarm notification system including a diagnostic measurement apparatus for measuring vital information of a patient body, and an alarm notification apparatus for notifying occurrence of an anomalous event in said patient body upon said occurrence thereof according to said vital information of said patient body input by said diagnostic measurement apparatus, said alarm notification system comprising:

said alarm notification apparatus including:

a processor configured to perform functions of:

monitoring said vital information of said patient body, to check whether said anomalous event has occurred to said patient body;

evaluating reliability of a result of detection of said anomalous event in a resulting from the monitoring of vital information; and selecting at least one addressee according to said reliability among plural predetermined addressees, and notifying said selected addressee of said occurrence of said anomalous event; and said alarm notification apparatus further comprising an error storage for storing error log data indicating a false detection when the anomalous event has not actually occurred, but where the monitoring of vital information indicates occurrence of the anomalous event, wherein in a case where said monitoring of vital information detects said anomalous event, said monitoring vital information function further obtains said reliability according to said error log data, wherein said monitoring vital information function outputs medical event record data, and wherein said evaluating reliability function acquires degree of coincidence between said medical event record data and said error log data recorded previously by comparison thereof, sets said reliability higher according to lowness of said degree of coincidence, and sets said reliability lower according to highness of said degree of coincidence.

11. An alarm notification method comprising steps of:

monitoring vital information of a patient body, to check whether an anomalous event has occurred to said patient body;

evaluating reliability of a result of detection of said anomalous event in said event checking step; and selecting at least one addressee according to said reliability among plural predetermined addressees, to notify said selected addressee of occurrence of said anomalous event said method further comprising: storing error log data indicating a false detection when the anomalous event has not actually occurred, but where the monitoring vital information step indicates occurrence of the anomalous event;

wherein in a case where said monitoring vital information step detects said anomalous event, said evaluating reliability step obtains said reliability according to said error log data, and wherein said monitoring vital information step further outputs medical event record data;

said evaluating reliability step acquires degree of coincidence between said medical event record data and said error log data recorded previously by comparison thereof, sets said reliability higher according to lowness of said degree of coincidence, and sets said reliability lower according to highness of said degree of coincidence.

\* \* \* \* \*